United States Patent [19]

Breipohl

[11] Patent Number: 5,516,937
[45] Date of Patent: May 14, 1996

[54] PROCESS FOR PREPARING AMINOETHYLGLYCINE

[75] Inventor: Gerhard Breipohl, Frankfurt, Germany

[73] Assignee: Hoechst Aktiengesellschaft, Frankfurt am Main, Germany

[21] Appl. No.: 402,383

[22] Filed: Mar. 13, 1995

[30] Foreign Application Priority Data

Mar. 14, 1994 [DE] Germany .......................... 44 08 530.3

[51] Int. Cl.⁶ .................................................. C07C 229/00
[52] U.S. Cl. ............................................................ 562/561
[58] Field of Search .............................................. 562/561

[56] References Cited

U.S. PATENT DOCUMENTS 2,387,735  10/1945  Bersworth .
4,528,397  7/1985  Shibamoto ............................. 562/561
4,598,079  7/1986  Beyerle ................................. 514/252
4,942,226  7/1990  Saari ..................................... 536/23

OTHER PUBLICATIONS

Heimer et al., "Synthesis of Analogs And Oligomers of N–(2–aminoethyl) glycine And Their Gastrointestinal Absorption In The Rat", Int. J. Peptide Protein Res. 23, (1984) pp. 203–211.

Tien et al., "The Preparation Of Substituted Hydrazines. A General Method For Preparing N–Substituted Glycines", J. Am. Chem. Soc. 77; pp. 6696–6698 (1955).

Primary Examiner—Michael L. Shippen
Attorney, Agent, or Firm—Finnegan, Henderson, Farabow, Garrett & Dunner

[57] ABSTRACT

A process is described for preparing aminoethylglycine from diaminoethane and glyoxylic acid by means of reductive amination.

5 Claims, No Drawings

PROCESS FOR PREPARING AMINOETHYLGLYCINE

Aminoethylglycine is an unusual amino acid which, inter alia, has an important role as a central structural component in the preparation of the so-called PNAs. The known preparation processes make use of the alkylation of diaminoethane with haloacetic acid derivatives (E. P. Heimer etal., Int. J. Peptide Protein Res. 23, 1984, 203–211) or the reaction of diaminoethane with formaldehyde and sodium cyanide (U.S. Pat. No. 2,387 735). However, in these said processes, salts are produced, as are undesirable by-products; furthermore, the working up is laborious. In addition, J. M. Thien etal. (Am. Soc. 77, 1955, 6996–6998) describes the synthesis of N-alkylglycines by reacting a monoamine with a glyoxylic ester and then hydrolyzing.

We have now found, surprisingly, that aminoethylglycine can be prepared, in a very simple process, from diaminoethane and glyoxylic acid by means of reductive amination. The process is notable in that it is simple to implement, salt-containing by-products are avoided and the crude product is easy to purify.

In the process for preparing aminoethylglycine, diaminoethane is mixed with glyoxylic acid, while cooling and stirring, in a ratio of 2–10:1, preferably 3–5:1, in water, a lower alcohol (such as methanol, ethanol or isopropanol, preferably methanol) or water/alcohol mixtures which contain approximately 30–60% of an above described alcohol, and this mixture is hydrogenated with hydrogen in the presence of a catalyst as reducing agent, such as, for example, palladium on charcoal, under standard pressure or a slightly elevated pressure (up to 0.5 bar), preferably at 0.3 bar. The solvent and the excess diaminoethane, which, where appropriate, may be employed once again in the reaction are then distilled off. The residue is coevaporated several times with toluene and then treated with a lower alkyl-alcohol, such as methanol or isopropanol, preferably methanol, for example at from room temperature to 60° C., preferably at from room temperature to 45° C., whereupon aminoethylglycine crystallizes out. A little water of crystallization may also possibly be present. The product results at a high level of purity, so that the crude product can be used directly for a subsequent reaction, for example to form the ester, in particular the methyl ester, with it being possible to employ, in the esterification, a quantity of alcohol which is markedly lower than that described in the literature, e.g. in E. P. Heimer et al., Int. J. Peptide Protein Res. 23, 1984, 203–211.

Some embodiments of the process which emphasize the advantages of the process as compared with the previously described processes, without, however, restricting it thereto, are described below.

Aminoethylglycine: ($C_4H_{10}N_2O_2$ 118.14)

EXAMPLE 1

4.6 g of glyoxylic acid monohydrate are dissolved in 200 ml of water, and 10.1 ml of diaminoethane are then added while cooling and stirring. 2 g of catalyst (10% Pd/C) are added to the mixture and hydrogenation takes place in a hydrogenation vessel under standard pressure and at room temperature. The reaction is complete when 1.3 l of hydrogen have been taken up. For the working up, the catalyst is filtered off with suction and the filtrate is concentrated to dryness in vacuo. The residue is subsequently distilled twice together with a little toluene, and the oily product, together with 100 ml of isopropanol, is left to stand overnight, during which time the product crystallizes out. The crystal slurry is thoroughly stirred once again and is then filtered off with suction and subsequently washed with a little isopropanol.

Yield: 4.18 g $R_F$(n-butanol/acetic acid/water/ethyl acetate=1:1:1:1): 0.2
MS(DCl): 119 [M+H]$^+$ NMR($D_2O$): 2.92–3.18 ppm(m, 4H, $CH_2$—$CH_2$); 3.35 ppm(s, 2H, $CH_2$—CO)

EXAMPLE 2

334 ml of diaminoethane are dissolved in 500 ml of ethanol, and a solution of 55.04 g of glyoxylic acid monohydrate in 100 ml of ethanol is then added slowly while cooling and stirring. 10 g of palladium on charcoal are then added to the mixture and hydrogenation is carried out in a hydrogenation vessel under standard pressure and at room temperature. After 10.9 l of hydrogen have been taken up, the reaction is complete and the catalyst is filtered off. The filtrate is concentrated in vacuo and the residue is subsequently distilled twice together with toluene; 1 l of isopropanol is added to the residue and the mixture is stirred thoroughly at approximately 45° C. The precipitate is filtered off with suction, then washed with a little isopropanol and dried in vacuo.

Yield: 47 g $R_F$(n-butanol/acetic acid/water/ethyl acetate=1:1:1:1): 0.2
MS (DCl): 119 [M+H]$^+$ NMR($D_2O$): 2.92–3.18 ppm(m, 4H, $CH_2$—$CH_2$); 3.35 ppm(s, 2H, $CH_2$—CO)

EXAMPLE 3

66.4 ml of ethylenediamine and 55.1 ml of an aqueous, 50% solution of glyoxylic acid are added, one after the other and while stirring and cooling, to a mixture of 500 ml of isopropanol and 500 ml of water. 2 g of palladium on charcoal are then added to the mixture and hydrogenation is carried out in a hydrogenation vessel under standard pressure and at room temperature. After 10.7 l of hydrogen have been taken up, the reaction is complete and the catalyst is filtered off. The filtrate is concentrated in vacuo and the residue is subsequently distilled twice together with toluene; 250 ml of isopropanol are added to the residue and the mixture is stirred thoroughly at approximately 45° C. The precipitate is filtered off with suction, then washed with a little isopropanol and dried in vacuo.

Yield: 48.7 g $R_F$(n-butanol/acetic acid/water/ethyl acetate=1:1:1:1): 0.2
MS (DCl): 119 [M+H]$^+$ NMR($D_2O$): 2.92–3.18 ppm(m, 4H, $CH_2$—$CH_2$); 3.35 ppm(s, 2H, $CH_2$—CO)

EXAMPLE 4

161.1 g of glyoxylic acid monohydrate are dissolved in 500 ml of water, 500 ml of methanol are then added, and 348.5 ml of diaminoethane are subsequently added while cooling and stirring. 15 g of catalyst (5% Pd/C) are added to the mixture and hydrogenation is carried out in a hydrogenation vessel under standard pressure and at room temperature. The reaction is complete after 37 l of hydrogen have been taken up. For the working up, the catalyst is filtered off with suction and the filtrate is concentrated to dryness in vacuo. The residue is redistilled three times together with toluene (approximately 200 ml), and the oily crude product is dissolved, with heating, in 300 ml of methanol; the solution is left to cool and then, after some seedling crystals have been added, left to stand in a cold room overnight, during which time the product crystallizes out. The crystal slurry is thoroughly stirred once again and then filtered off with suction; it is subsequently washed twice with approximately 80 ml of ice-cold methanol and the colorless, crystalline product is dried in a desiccator ($N_1$). Additional product can be isolated from the mother liquor by concentrating the latter to approximately 300 ml and adding approximately 600 ml of isopropanol and a few seedling crystals. After this mixture has been allowed to stand overnight in a cold room, further crystalline product is obtained which is filtered off with suction and subsequently washed with a little ice-cold methanol Yield: $N_1$: 104.9 g; $N_2$: 24.3 g; Total yield: 129.2 g $R_F$(n-butanol/acetic acid/water/ethyl acetate=1:1:1:1): 0.2 MS (DCl): 119 $[M+H]^+$ NMR($D_2O$): 2.92–3.18 ppm(m, 4H, $CH_2$—$CH_2$); 3.35 ppm(s, 2H, $CH_2$—CO)

EXAMPLE 5

1.80 l of diaminoethane are dissolved in 2.61 l of methanol, and 840 g of glyoxylic acid monohydrate, dissolved in 2.61 l of water, are then slowly added while cooling and stirring. An autoclave is filled with the mixture, 78 g of catalyst (Pd-animal charcoal) are added, and the mixture is hydrogenated at room temperature and under 0.3 bar hydrogen pressure. The reaction is complete after 200 l of hydrogen have been taken up. For the working up, the catalyst is filtered off with suction and the filtrate is concentrated to dryness in vacuo. The residue is subsequently distilled twice together with toluene (approximately 1 l), and the resulting yellow oil is taken up in 1.56 l of methanol; this mixture is stirred, while being cooled, for 3 h and is then filtered with suction. The material which has been filtered off is washed with a little ice-cold methanol and the colorless, crystalline product is dried in a desiccator ($N_1$).

Additional product can be isolated from the mother liquor by concentrating the latter down to approximately 1.5 l and adding approximately 3 l of isopropanol and a few seedling crystals. After this mixture has been left to stand overnight in a cold room at 4° C., additional crystalline product is obtained which is filtered off with suction, then washed with a little ice-cold methanol and dried in a desiccator ($N_2$).

Yield: $N_1$: 408 g; m p: 149°–153° C. decomp.; $N_2$: 180 g; m.p.: 152°–154° C., decomp. Total yield: 588 g $R_F$(n-butanol/acetic acid/water/ethyl acetate=1:1:1:1): 0.2 MS (DCl): 119 $[M+H]^+$ NMR($D_2O$): 2.92–3.18 ppm(m, 4H, $CH_2$—$CH_2$); 3.35 ppm(s, 2H, $CH_2$—CO)

EXAMPLE 6

Aminoethylglycine methyl ester dihydrochloride: ($C_5H_{12}N_2O_2 \cdot 2HCl$ 205.09)

460 g of aminoethylglycine are introduced into 14 l of methanol, and 500 g of HCl gas are then passed into the suspension. The mixture heats up and is then maintained under reflux for a total of 8 h. After that, the reaction is complete and the mixture is cooled down to 0° C. and then stirred at this temperature for 3 h. Filtering off with suction takes place through a suction filter and the product is dried in vacuo. 716 g of colorless crystals are obtained with a melting point of 190°–192° C. $R_F$(n-butanol/acetic acid/water/ethyl acetate=1:1:1:1): 0.3 MS (DCl): 133 $[M+H]^{30}$ NMR($D_2O$): 3.42–3.65 ppm(m, 4H, $CH_2$—$CH_2$); 3.92 ppm(s, 3H, CO—$OCH_3$), 4.18 ppm(s, 2H, $CH_2$—CO)

I claim:

1. A process for preparing aminoethylglycine, wherein diaminoethane is mixed with glyoxylic acid, while cooling and stirring, in a ratio of 2–10:1, in water, a lower alcohol or water/alcohol mixtures, and this mixture is hydrogenated with hydrogen, in the presence of a catalyst as reducing agent, under standard pressure or a slightly elevated pressure, the solvent and the excess diaminoethane are then distilled off, and the residue is coevaporated together with toluene and treated with a lower alkyl-alcohol, whereupon aminoethylglycine crystallizes out.

2. The process as claimed in claim 1, wherein palladium on charcoal is employed as the catalyst.

3. The process as claimed in claim 1, wherein diaminoethane and glyoxylic acid are employed in a ratio of 3–5:1.

4. The process as claimed in claim 1, wherein hydrogenation is carried out at 0.3 bar.

5. The process as claimed in claim 1, wherein the resulting crude product is crystallized by being treated with methanol.

* * * * *